(12) United States Patent
Diaz et al.

(10) Patent No.: US 6,980,716 B1
(45) Date of Patent: Dec. 27, 2005

(54) COHERENT EVANESCENT WAVE IMAGING

(75) Inventors: Rodolfo E. Diaz, Phoenix, AZ (US);
Ampere A. Tseng, Phoenix, AZ (US);
Karl S. Booksh, Gilbert, AZ (US); Jose Menendez, Tempe, AZ (US);
Sethuraman Panchanathan, Gilbert, AZ (US); Michael Wagner, Chandlek, AZ (US)

(73) Assignee: Arizona Board of Regents, Tempe, AZ (US)

( * ) Notice: Subject to any disclaimer, the term of this patent is extended or adjusted under 35 U.S.C. 154(b) by 224 days.

(21) Appl. No.: 10/112,006

(22) Filed: Mar. 29, 2002

Related U.S. Application Data

(60) Provisional application No. 60/280,644, filed on Mar. 30, 2001.

(51) Int. Cl.$^7$ .................................................. G02B 6/42
(52) U.S. Cl. ......................................................... 385/30
(58) Field of Search ................................. 385/129, 141, 385/130–131, 14; 356/445; 359/296

(56) References Cited

U.S. PATENT DOCUMENTS

| | | | | |
|---|---|---|---|---|
| 4,497,544 | A | * | 2/1985 | Mitchell et al. ............. 359/244 |
| 6,144,035 | A | * | 11/2000 | Piper et al. .................. 250/372 |
| 6,157,124 | A | * | 12/2000 | Wakasono ................... 313/461 |
| 6,157,125 | A | * | 12/2000 | Chigusa et al. ............. 313/480 |
| 6,265,021 | B1 | * | 7/2001 | Black et al. ................. 427/131 |
| 6,529,277 | B1 | * | 3/2003 | Weitekamp ................. 356/445 |
| 6,539,156 | B1 | * | 3/2003 | Dickson et al. ............. 385/129 |
| 6,590,647 | B2 | * | 7/2003 | Stephenson ................. 356/301 |
| 6,680,211 | B2 | * | 1/2004 | Barbera-Guillem et al. 436/533 |
| 6,727,071 | B1 | * | 4/2004 | Dunlay et al. ............. 435/7.21 |
| 6,778,316 | B2 | * | 8/2004 | Halas et al. ................. 359/296 |
| 2002/0025490 | A1 | * | 2/2002 | Shchegolikhin et al. ..................... 430/270.15 |
| 2003/0147616 | A1 | * | 8/2003 | Dickson et al. ............. 385/129 |

OTHER PUBLICATIONS

Y. Martin, S. Rishton, H. K. Wickramasinghe, "Optical data storage read out at 256 Gbits/in." *Appl. Phys. Lett.* 71, 1 1–3 (Jul. 1997).

H. D. Yang, R. Diaz, N. G. Alexopoulos, "Reflection and transmission of waves from multilayer structures with planar–implanted periodic material blocks" *J. Opt. Soc. Am. B* 14, 10 2513–2521 (Oct. 1997).

C. R. Simovski, S. A. Tretyakov, A. H. Sihvola, M. M. Popov, "On the surface effect in thin molecular or composite layers" *Eur. Phys. J. AP* 9, 195–204 (2000).

M. Alejandro–Arellano, T. Ung, A. Blanco, P. Mulvaney, L. M. Liz–Marzan, "Silica–coated metals and semiconductors, stabilization and nanostructuring" *Pure Appl. Chem.* 72, 1–2 257–267 (2000).

(Continued)

*Primary Examiner*—Joseph Williams
*Assistant Examiner*—Peter Macchiarolo
(74) *Attorney, Agent, or Firm*—Gallagher & Kennedy, P.A.; Thomas D. MacBlain

(57) ABSTRACT

Methods and apparatus for gathering image information from nanostructures includes a composite waveguide of conductive nanoparticles in a dielectric medium. The waveguide is irradiated with preferably coherent blue light to form a slow surface wave. The evanescent wave that is the "tail" of the surface wave exists outside the waveguide contiguous to its surface. The nanostructures are located to encounter the evanescent wave. The slowing of the wave that occurs in the waveguide reduces the wave's speed and wavelength sufficiently such that nanostructures can be imaged. Upon encountering the evanescent wave, the nanostructures radiate. This radiation causes a backward scattering from the structures and a forward perturbation of the wavefront of the surface wave. From the scattering and perturbation information about the physical characteristics of the nanostructures sufficient to form an image is derived.

65 Claims, 6 Drawing Sheets

OTHER PUBLICATIONS

L. A. Obando, K. S. Booksh, "Tuning dynamic range and sensitivity of white–light, multimode, fiber–optic surface plasmon resonance sensors" *Anal. Chem.* 71,22 5116–5122 (Nov. 15, 1999).

J. Memendez, "Phonons in GaAs–Al$_x$Ga$_{1-x}$As superlattices" *Journal of Luminescence* 44, 285–314 (1989) North–Holland, Amsterdam.

O. Fatemi, S. Panchanathan, "Fractal engine: an affine video processor core for multimedia applications" *III Transactions on Circuits and Systems for Video Technology* 8, 7 892–908 (Nov. 1998).

C. D. Poweleit, A. Gunther, S. Goodnick, J. Memendez, "Raman imaging of patterned silicon using a solid immersion lens" *Appl. Phys. Lett.* 73, 16 2275–2277 (Oct. 19, 1998).

M. Labardi, S. Patane, M. Allegrini, "Artifact–free near–field optical imaging by apertureless microscopy" *Appl. Phys. Lett.* 77, 5 621–623 (Jul. 31, 2000).

R. E. Diaz, J. T. Aberle, W. E. McKinzie, "TM mode analysis of a sievenpiper high–impedance reactive surface" *IEEE* 7803–6369 327–330 (Aug. 2000).

S. A. Maier, M. L. Brongersma, P. G. Kik, S. Meltzer, A. A. G. Requicha, H. A. Atwater, "Plasmonics—a route to nanoscale optical devices" *Adv. Mater.* 13,19 1501–1505 (Oct. 2, 2001).

S. A. Maier, M. L. Brongersma, H. A. Atwater, "Electromagnetic energy transport along arrays of closely spaced metal rods as an analogue to plasmonic devices" *Appl. Phys. Lett.* 78, 1 16–18 (Jan. 1, 2001).

* cited by examiner

COHERENT EVANESCENT WAVE IMAGING

RELATED APPLICATIONS

This application is related to and claims priority from U.S. Provisional Application Ser. No. 60/280,644 entitled Coherent Evanescent Wave Imaging of Rudolfo Diaz, Ampere Tseng, Karl Booksh, Jose Menendez, Michael Wagner and Sethuraman Panchanathan, filed Mar. 30, 2001.

FIELD OF THE INVENTION

This invention relates to methods and apparatuses for observing the characteristics of nanostructures and more particularly methods and apparatus for producing images of nanostructures by causing the nanostructures to encounter a slow, electromagnetic, evanescent wave formed by a slowed electromagnetic surface wave in a waveguide irradiated with electromagnetic energy having a free-space wavelength substantially greater than that of the resultant slow wave in the medium of the wave guide.

BACKGROUND OF THE INVENTION

There has been considerable interest in understanding and developing nanostructures, but this has been hampered by limitations on observation that these structures impose by nature of their size.

Whereas in the past, various microscopy techniques have been sufficient to detect defects of a surface at the nanostructure level, or the mere presence of a nanostructure, these have been inadequate to provide characteristics of the nanostructure such as would permit development of images or details of physical features, such as dimensions, shape and other characteristics.

One daunting difficulty in characterizing nanostructures based on observation has been the wavelength of light. At 488 nm., even blue light has a wavelength in free space (or air) that is too long for use in imaging objects where those objects have dimensions that may range from just a few nm. to several times the wavelength of the light. Ultraviolet light degrades too readily under most conditions to afford a reasonable alternative. In microscopy it is known to locate a specimen in a drop of liquid and to bring the object lens of the microscope into contact with the liquid to take advantage of the reduction in the speed of light that occurs within the liquid and the commensurate reduction in wavelength of the light impingent on the specimen. This technique is not suitable for imaging nanostructures. First, the reduction in wavelength is not sufficient to permit imaging of specimens or structures having dimensions of just a few nm. Second, nanostructures within a liquid are likely to have their observable characteristics and their observable motion altered or distorted. This may occur by the liquid pressure, by dissolving, by chemical reaction or by other interactions of the liquid and the nanostructure. To substantially reduce wavelength, blue light at 488 nm. would need to be used in a medium such as diamond. This would slow the speed of the light by a factor of two, consequently reducing the wavelength by half. Again, this is both impractical and insufficient. The nanostructures being examined cannot be situated in a diamond medium, and halving the 488 nm. wavelength is still not a sufficient reduction. For effective imaging of nanostructures a reduction of the 488 nm. wavelength of blue light by a factor of ten would be desirable.

In *Plasmonics-A Route to Nanoscale Optical Devices*, Advanced Materials, 13, No. 19, Oct. 13, 2001 (Wiley-VCH Verlag GmbH), Maier et al. teach using gold nanoparticles with diameters between 30 and 50 nm., spaced "a few tens of nanometers apart," as building blocks for "plasmon waveguides." This publication is incorporated herein by reference. The speed of wave propagation at the center of the operating band along the series of spaced nanoscale spheres of Maier et al. is $\frac{1}{10}$ the free-space speed of the electromagnetic radiation employed. Consequently, the wavelength is $\frac{1}{10}$ that of the free-space wavelength. Maier et al. do not suggest using the speed reduction for light wavelength reduction enabling examination of nanostructures. Rather, Maier et al. suggest optical wave guides fashioned into optical path "Ls," "Ts" and switches for use in optical circuitry, so slowing the speed of light is not an objective. And, in fact, Maier et al. mention they are seeking the fastest such propagation velocity, whereas we desire the slowest. Maier et al. do not suggest suspension of particles in a dielectric medium.

BRIEF DESCRIPTIONS OF THE INVENTION

In accordance with this invention there is provided methods and apparatuses for determining characteristics of one or more nanostructures using electromagnetic radiation. A slow moving electromagnetic wave is used to illuminate the nanostructure. In accordance with one aspect of the invention nanostructures are positioned to encounter an evanescent electromagnetic wave that is a characteristic of a slow electromagnetic surface wave. Effects of electromagnetic interactions between the evanescent wave and the one or more nanostructures are observed. These effects may be an electromagnetic scattering effect or a perturbation of the wavefront of the evanescent electromagnetic wave that encounters the nanostructure.

The evanescent electromagnetic wave can be produced by irradiating a wave guide having a boundary surface between a first, internal medium and a second, external medium such that a slow electromagnetic surface wave is produced in the wave guide at the surface with a characteristic evanescent electromagnetic wave in the second medium contiguous to the surface. The nanostructure or nanostructures are located in the second medium proximate the waveguide surface at which the surface wave is produced.

To produce the evanescent wave, the waveguide is irradiated by a electromagnetic energy having a wavelength in the medium of the wave guide that may be shorter than its wavelength in free space by a factor of ten or more. In a preferred embodiment the electromagnetic energy is blue light having a wavelength in free space of substantially 488 nm. The electromagnetic energy is directed through the medium of the waveguide in such a way as to create the surface wave. The coupling from the incident wave to the surface wave is typically accomplished via discontinuities on the surface such as a line grating or, as illustrated in FIG. 1, the end of the waveguide itself. In the preferred embodiment, this coupling is accomplished by a laser illuminating a conductive sphere or particle that is optically coupled to the waveguide. This creates a plasmon in the sphere or particle serving as a point source of coherent light for the waveguide.

The evanescent wave or "tail" portion of the surface wave that is produced in the second medium, outside of the waveguide and contiguous to its surface decays exponentially with distance from the surface. The electromagnetic energy directed through the medium of the wave guide is preferably coherent. This enables detection of effects of the interaction of the evanescent wave and the nanostructures that may include diffraction, scattering backward in a direction that is the reverse of the direction of wave propagation, and perturbation of the wavefront in the direction of wave propagation, a degradation or diminishing of the coherent wave that is caused by passage over the nanostructures. This latter effect may be thought of as the inverse of the backward scattering echo that occurs.

In one preferred embodiment the evanescent wave portion of a coherent collimated surface wave is split into a reference wave and a nanostructure-illuminating wave, the nanostructures are illuminated by the nanostructure-illuminating wave, and the split waves are brought together. Additive reinforcement and subtractive interference that occurs when the two waves combine give image information regarding the nanostructures. As used herein, the term "electromagnetic" and "electromagnetic energy" wave and the like are not limited to electric waves or waves in just the radio frequency or microwave ranges, but include as well light waves.

"Nanostructures" means structures having dimensions measured in nanometers that may range from just a few nanometers to less than a thousand nanometers, or put another way from a dimension very significantly less than the wavelength in free space of electromagnetic energy used to observe the nanostructure up to about 100 multiples of the wavelength in free space of that electromagnetic energy. A nanostructure could be a bacterium or a "nanomachine." As used herein, referring to the nanoparticles, "cross-sectional dimension" means the particles' greatest cross-sectional dimension.

The above and further objects and advantages of the invention will be better understood from the following detailed description of at least one preferred embodiment of the invention, taken in consideration with the accompanying drawings.

DESCRIPTION OF PREFERRED EMBODIMENTS

Figure 1:
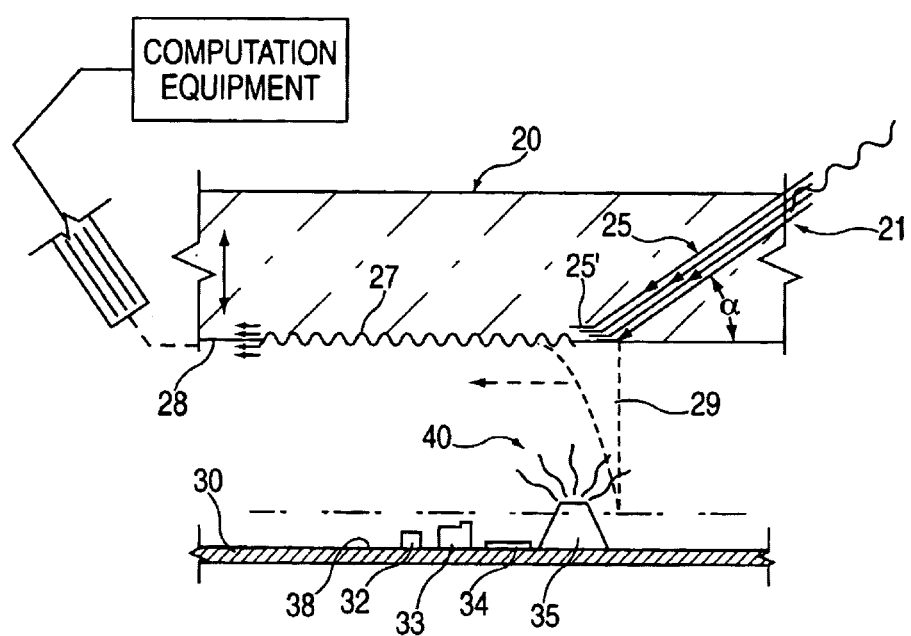
FIG. 1 is a fractional diagrammatic illustration of a nanostructure imaging arrangement showing a wave guide with a surface wave, an evanescent wave and nanostructures being imaged.

Turning to FIG. 1, a cross section of a portion of an instrument for detecting physical characteristics of nanostructures is diagrammatically illustrated for purpose of explanation. A surface wave is produced at the surface of a waveguide. The surface wave is an electromagnetic slow wave that does not travel in free space but is bound to a surface. The wave exists at the boundary between a medium (the waveguide) and the free space, air or other medium outside the waveguide boundary. Such a wave has associated with it an exponentially decaying tail located outward of the waveguide in the air or free space bounded by the surface of the guide. The free space portion of the surface wave thus created in the space proximate the waveguide's surface is termed an "evanescent wave." The wave does not propagate away from the boundary, but it is detectable. It does not radiate, but an object placed in the wave will radiate. As graphically illustrated in FIG. 1, a waveguide 20 is irradiated with light 25 to create such a surface wave. At a coupling discontinuity 21, light is coupled to the waveguide. In the wave guide, which is of a light transmissive medium with a higher index of refraction than air, the light is directed to the medium-air interface 28 at the coupling discontinuity so as to generate the surface wave through the near fields of the discontinuity's electromagnetic scattering.

Figure 3:
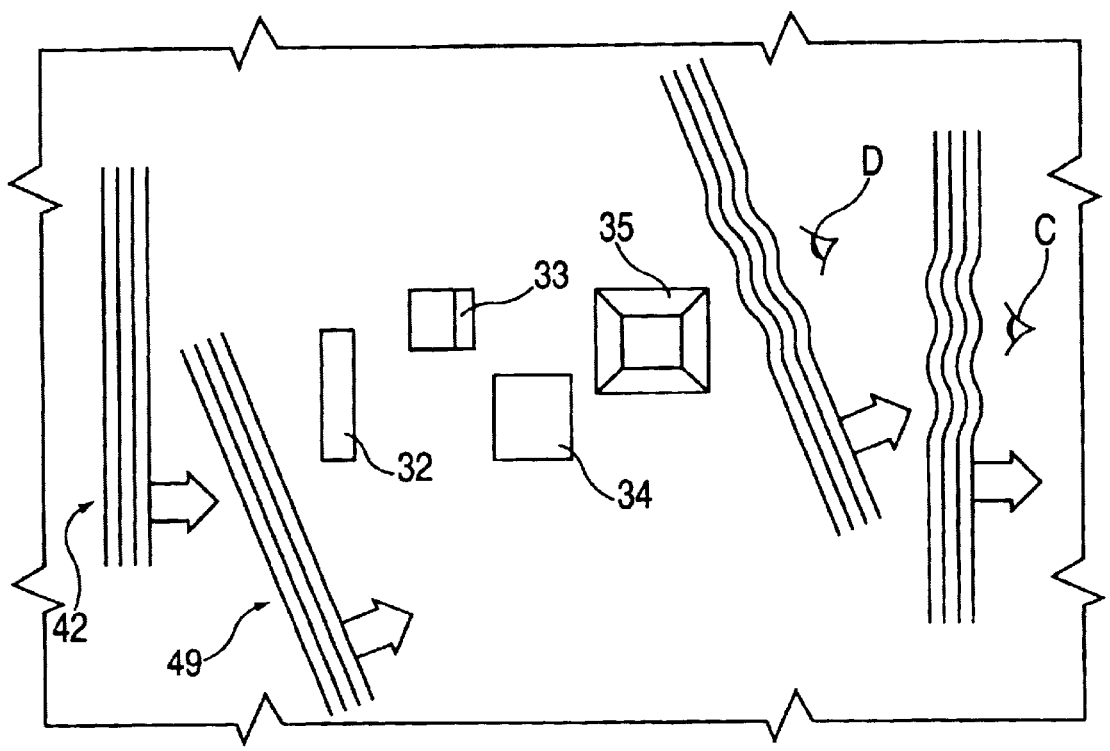
FIG. 3 is a fragmentary, diagrammatic planar view like FIG. 2 and illustrates diagrammatically a further technique for the derivation of structural information by varying the direction of illumination of the nanostructures with coherent light.

A number of techniques are used to produce an image of structure using the phenomenon of the evanescent wave. A metal substrate 30 has nanostructures 32, 33, 34 and 35 projecting from its upper surface 38. The waveguide 20 and substrate 30 should be relatively moveable toward and away from one another. Here, movement of the waveguide as indicated toward and away from the substrate is assumed as indicated by the unnumbered arrow on the guide. At 25' the light propagated along the surface is the surface wave, graphically illustrated at 27. The associated evanescent wave is graphically illustrated at 29, diminishing exponentially in the direction away from and normal to the surface 28. As it is moved toward the metal surface 38 the structure 35 interacts with the evanescent wave 29 and radiates as indicated at 40. In other words, the wave 29 excites a current or plasmon in the structure 35 which accordingly radiates. That radiation can be detected. It causes scattering backward from the direction of propagation of the surface wave and its attendant tail (to the right as illustrated in FIG. 1) and a decay or degradation in the surface wave 27 going forward (to the left in FIG. 1). At the separation distance of the substrate 30 and the waveguide 20 shown in FIG. 1, only the tallest nanostructure 35 is detected. The structures 32, 33 and 34 are shorter and are not irradiated by the evanescent wave. This, then, is information concerning the relative heights of the nanostructures 32, 33, 34 and 35. Moving the guide 20 and substrate 30 closer, the nanostructure 33 will next be detected. If the evanescent wave has planar wave fronts 25 progressing across structures 32, 33, 34 and 35, for example, as shown in FIG. 3, the structures will cause scattering of the evanescent wave. That scattering, backward from the direction of wave propagation, is the echo referred to above. In the wave going forward, a perturbation of the evanescent wave is the inverse of the scattering echo. This is the effect notes in the forward direction of wave propagation. In other words, as the evanescent wave proceeds, the planar wave front of the slow, surface wave 27 will now be altered by the radiation from the structure 40 caused by its encounter with the evanescent wave.

By making the surface wave 27 coherent, the irradiant "scattering" from the nanostructure is made coherent. As diagrammatically illustrated in FIG. 2, it then becomes possible by moving the location of observation to detect interference from out-of-phase light reflected from the nanostructures at, say, location A and reinforcement of in-phase reflected light from the nanostructures at, say, location B. The effect is analogous to a hologram in which the observer's location affects the observable image through interference and reinforcement of coherent light. At observation location C the wavefronts indicated by 45 are seen to be perturbed or degraded by their interaction with the nanostructures 32, 33, 34 and 35 as indicated schematically at 47. The information observed at C is the inverse of the backwave scattering or echo. The technique by which the echoes received at A, B, and a multiplicity of other similarly disposed locations, can be inverted to obtain an image of the scattering objects is known as ISAR (Inverse Synthetic Aperture Radar).

Figure 2:
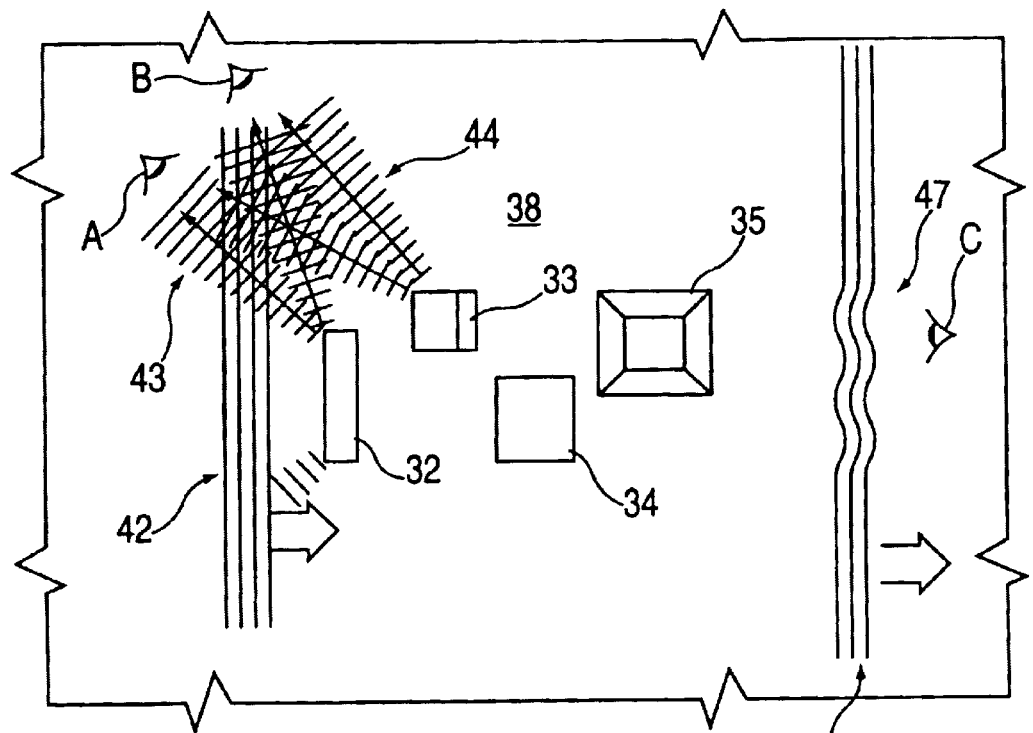
FIG. 2 is a fragmentary, diagrammatic planar view of nanostructures illuminated by coherent light and illustrates diagrammatically the derivation of structure information from backward scattering and forward degradation of the wave front of the coherent light.

In FIG. 3 a similar technique to that employed in FIG. 2 at A and B is used to image the structure 32, 33, 34 and 35 in the forward direction (to the right in FIG. 3). The observer's position is varied from C to D as shown. The direction of propagation of the surface and evanescent wave is changed from 42 to 49. By observing the disturbance of the wave fronts at various locations as the field traverses the structures at varying angles, an image can be created from the composite information gathered. Techniques similar to those used in tomography may be used here. It will be appreciated that numerous such observations are contemplated, not with the naked eye, but with instrumentation to gather and computer software and hardware suitable to store and compile the information thus garnered.

Figure 4:
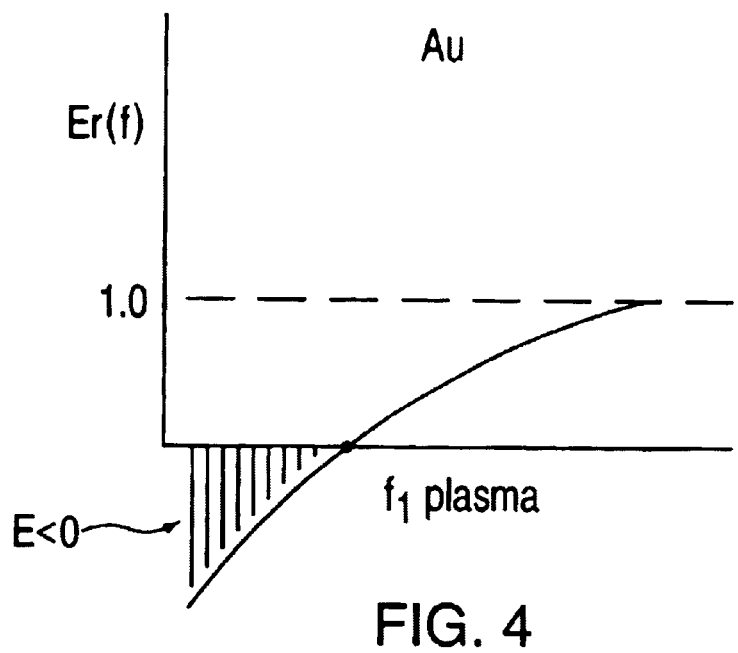
FIG. 4 is a plot of permittivity versus frequency for gold.
Figure 6:
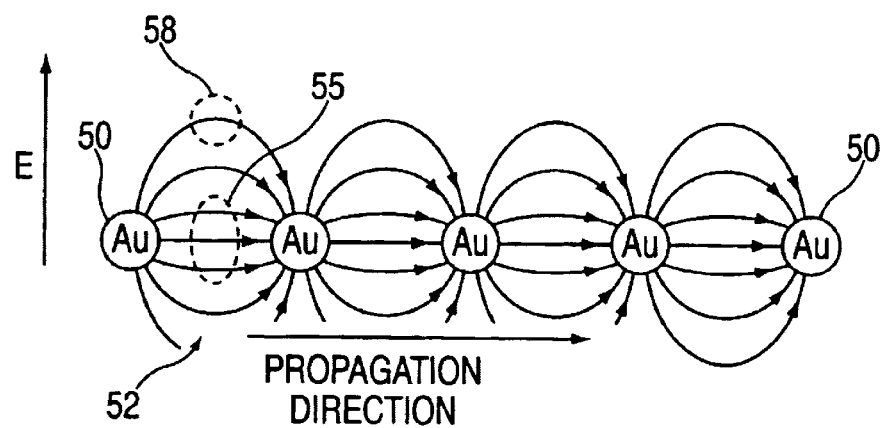
FIG. 6 is a diagrammatic illustration of a waveguide utilizing a single row of spaced gold nanoparticles as described by Maier, et al.

As noted above, the wavelength of the light is an important factor. It is desirable to slow the speed of light to $1/10^{th}$ or less of its speed in free space. That has the effect of reducing the wavelength by a factor of 10 since $\lambda_0 = C_0/F_0$. However ordinary dielectrics cannot be used to effect such a reduction in wavelength. Even if the permittivity ($\in$) of the medium is increased by a factor of 10 the light velocity is only related to the square root of $\in$ and so will not vary nearly as much. A velocity decrease to only approximately $1/3$ of the original velocity is thus achieved. Consequently dispersive structures have been formulated to "fool" the wave. FIG. 4 plots $\in$ in gold (Au) versus frequency. $\in$ crosses the zero axis at a point $f_1$. Where $\in$ is less than zero, as indicated in FIG. 4, very slow guided waves result. Maier et al. show that a propagated light wave along a chain of gold nanobeads or particles as shown in FIG. 6 can theoretically reduce the velocity of wave propagation by a factor of 10. In the article cited above, Maier et al. were not interested in reducing speed, but in increasing speed for the purpose of improving light circuitry. High resolution nano imaging was not discussed. A preferred embodiment of this invention uses a material made up of gold globes or particles coated with silicon dioxide $SiO_2$ that bind the gold particles in a matrix.

Figure 5:
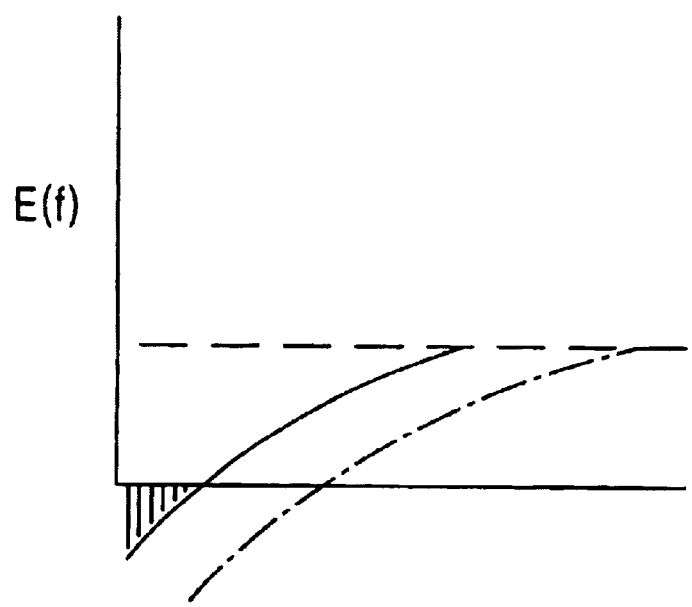
FIG. 5 is a plot like FIG. 4 and shows the change in the plot using a waveguide of gold particles dispersed in silicon dioxide according to one aspect of the invention.
Figure 7:
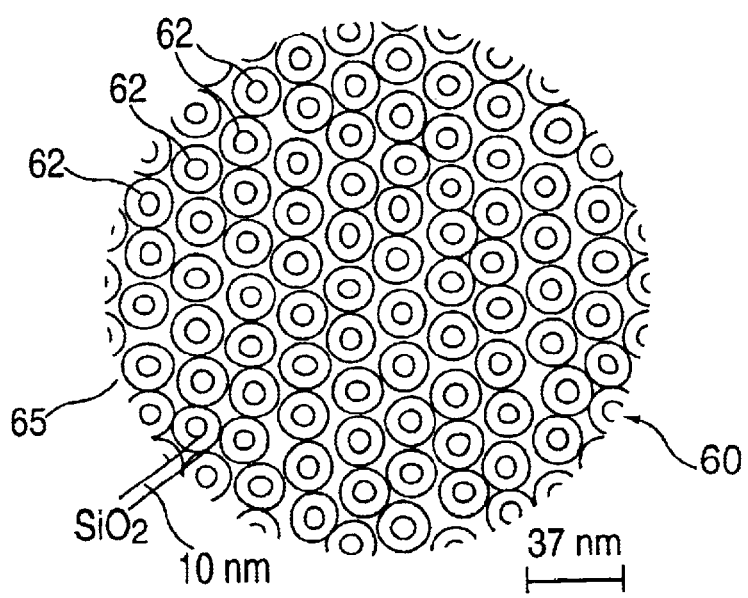
FIG. 7 is a diagrammatic enlarged, fragmentary planar view of a waveguide in accordance with this invention.

At FIG. 6 a field produced in a waveguide like the theoretical line of gold particles described in the above article of Maier et al. is shown graphically. A strongest portion 55 of the field 52 is within the guide which here is from one gold particle 50 to the next. However an evanescent field 58 with the configuration shown from particle to particle is the characteristic exponentially diminishing field that occurs in such a structure. Changing the spacing between the particles and altering the permittivity of the interstitial medium permits tuning of the guide to vary the field. In accordance with this invention, then, a composite guide 60 is provided, as shown in FIG. 7. The exemplary waveguide 60 has an array of gold particles 62 that have cross-sectional dimensions of approximately 10 nm. and are spaced apart approximately 37 nm. in a $SiO_2$ binder 65. A waveguide thus formed has an apparent permittivity altered as illustrated the full line plotted in FIG. 5.

Figure 8:
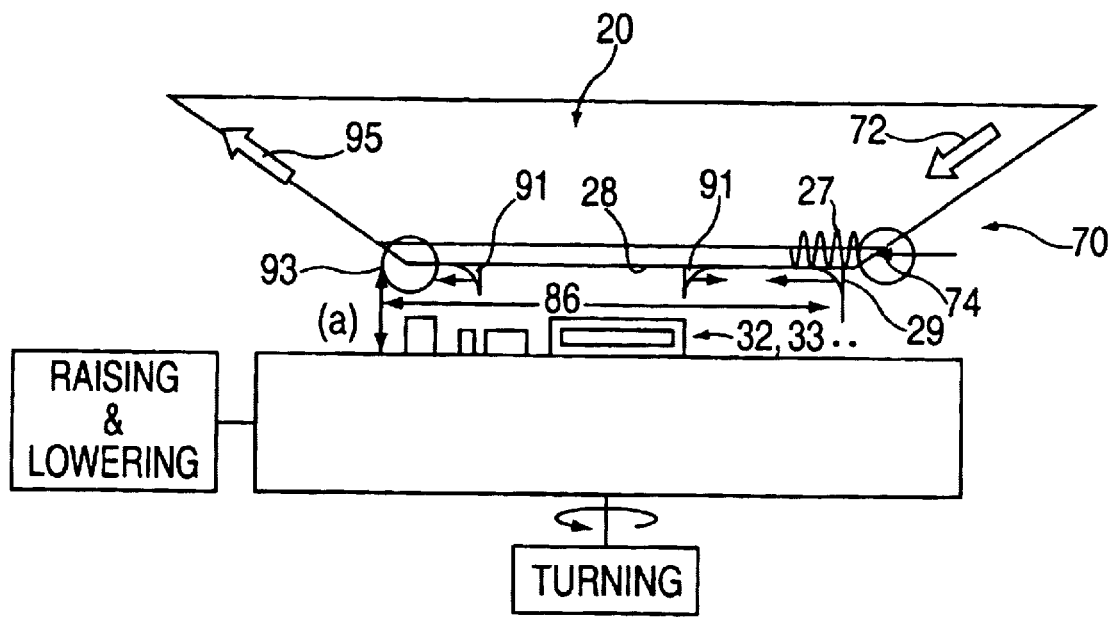
FIG. 8 is an enlarged, diagrammatic, side elevation view of a transducer for imaging nanostructures in accordance with the invention and shows the nanostructures located on a surface below a waveguide of the kind illustrated in FIG. 7.
Figure 9:
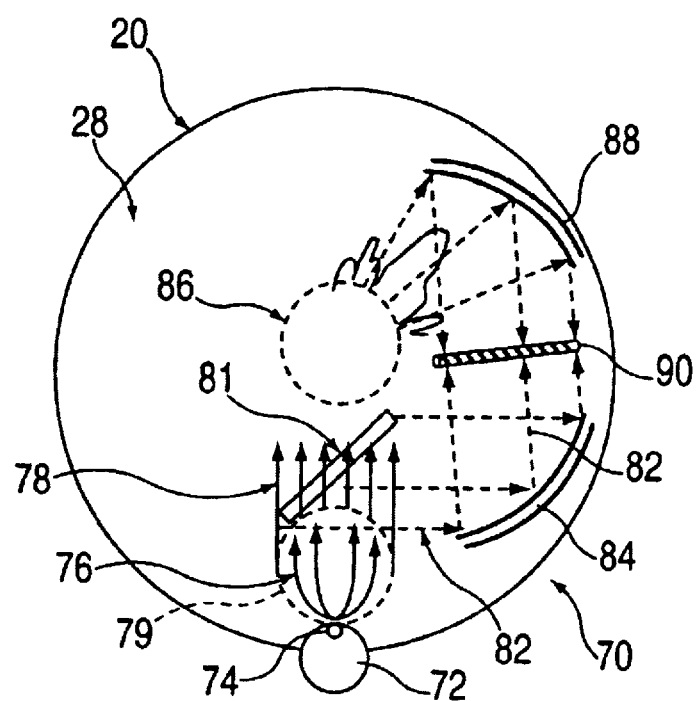
FIG. 9 is a bottom plan view of the waveguide undersurface of the transducer of FIG. 8 and shows wave directing provisions of the waveguide and a detector for outputting information relating to nanostructures.

One preferred embodiment of an imaging transducer 70 is shown in FIGS. 8 and 9. A laser 72 is incident on a conductive bead or particle 74 to produce a surface plasmon point source as is common practice in a technique known as surface enhanced Raman scattering. The emerging light 76 is collimated at 78 by a Luneberg lens 79. The collimated coherent beam 78 is split by a beam splitter 81 to produce a reference wave 82 directed to a first Bragg mirror 84 which may be, for example, a projection from the surface 28 of the waveguide 20 that is two gold particles in height. The portion of the coherent collimated beam 78 passing through the beam splitter 81 interacts with the structure being imaged in an interaction region 86 and impinges on a second Bragg mirror 88. The two Bragg mirrors direct their reflected waves to a novel detector array 90. The detector array 90 is a linear series of gold nanoparticles each coated with a different fluorescent material chosen to fluoresce when illuminated so as to produce different wavelengths of emitted light. Impinging light across the detector thus produces a color coded signature or profile. Where the two combined coherent waves interfere the fluorescent particle remains dark. Where they reinforce light of a particular wavelength is emitted. The variation in light along the length of the detector can be plotted based on the colors of emissions and this provides information on the features of the structures under observation. Alternatively the pattern of light reinforcements and interferences may be projected and enlarged to derive this information.

Surface and target nanostructures for the creation and characterization of the proposed imaging system can be manufactured using a combination of nano-deposition and nano-machining processes. An ultrahigh vacuum evaporation system used for thin-film deposition can be adopted for forming the nano-scale substrate of multi-material layered structures. The multi-layer substrates are then further shaped or sculpted by a nano-machining process to their final configurations. Equipment capable of producing beam spot sizes from 50 to 500 nm. with current densities up to 5 A/cm2 can be used to accomplish the nano-machining. Combinations of ion species, e.g., PdAsB, AuSiBe, or Ga, can be obtained from liquid metal ion sources.

The Bragg mirror is a known device. It consists of a series of alternating transparent obstacles with varying index of refraction, spaced one-half wavelength apart. Each obstacle by itself has negligible effect on an incident wave, but the combined scattering from 20 or more layers can approach 100% reflection. In our preferred embodiment, it has spheres or particles located half a wave length apart so as to interact with a desired wave length and reflect 100% of light at that wavelength. The beam splitter 81 may be a line of spheres or particles that are two spheres high (to simulate a pellicle) or it may be another integral part of the topography of the surface 28 of the waveguide 20. In FIG. 8 the "tail" 29 of the coherent, slow, surface wave 27 is shown as are the nanostructures 32, 33, 34 and 35. Scattering echo waves and perturbations are indicated at 91. The coherent, nanostructure-illuminating wave is output at 93 and directed at 95 to the detector 90 of FIG. 9 where it interacts with the coherent, slow surface wave that is the reference wave 82 (FIG. 9).

Techniques currently used for imaging structures with waves such as, for example, Tomography, Nomarski microscopy, and Synthetic Aperture Radar, can be used to reconstruct the entire image field. Fusion of images obtained by different techniques and at different wavelengths will yield a rich multi-spectral characterization of the subject nanostructures.

The foregoing descriptions of at least one preferred embodiment are exemplary and not intended to limit the claimed invention. Obvious modifications that do not depart from the spirit and scope of the invention as claimed will be apparent to those skilled in the art.

We claim:

1. A method of gathering information concerning nanostructure characteristics including:
   (a) providing a waveguide of a first medium having a surface bounding a second medium;
   (b) irradiating the waveguide with an electromagnetic wave to produce a surface wave at the surface bounding the second medium and an evanescent wave in the second medium contiguous with the surface;
   (c) locating at least one nanostructure in the second medium proximate the surface where it will encounter the evanescent wave; and
   (d) determining a characteristic of the nanostructure by observing at least one effect of electromagnetic interactions between the evanescent wave and the at least one nanostructure.

2. The method according to claim 1, wherein step (b) comprises irradiating the waveguide with coherent electromagnetic energy.

3. The method according to claim 2, wherein step (d) comprises detecting one or more of scattering of electromagnetic surface wave energy due to perturbation of the evanescent wave as a result of impingement of the evanescent wave on the at least one nanostructure.

4. The method according to claim 2, wherein step (d) comprises detecting one or more of scattering of electromagnetic surface wave energy in a direction backward of the direction of propagation of the surface wave and perturbation of a wavefront in the direction of surface wave propagation.

5. The method according to claim 2, wherein step (d) comprises observing at least one of subtractive interference and associative reinforcement of the surface wave with electromagnetic effects of the impingement of the evanescent wave on the at least one nanostructure.

6. The method according to claim 1, further comprising repositioning the at least one nanostructure angularly with respect to the direction of propagation of the evanescent wave, and step (d) comprising observing the effect of electromagnetic interactions between the evanescent wave and the at least one nanostructure in each relative angular position of the at least one nanostructure and incident evanescent wave.

7. The method according to claim 1, wherein step (a) comprises providing a waveguide including an array of particles of conductive material spaced apart in a binder having a higher dielectric constant than the material of the particles, the particles being of a cross-sectional dimension in the range from 1 to 100 nm.

8. The method according to claim 7, wherein the particles are of a noble metal.

9. The method according to claim 7, wherein the particles are gold.

10. The method according to claim 7, wherein the particles are spaced apart at distances in a range of 1 to 100 nm.

11. The method according to claim 10, wherein the particles have a cross-sectional dimension in a range from 10 to 50 nm.

12. The method according to claim 11, wherein the particles are spaced apart by distances in a range of 10 to 50 nm.

13. The method according to claim 7, wherein the binder is $SiO_2$.

14. A method of gathering information concerning nanostructure characteristics including:
   (a) providing a waveguide of a first medium having a surface bounding a second medium;
   (b) irradiating the waveguide with an electromagnetic wave to produce a surface wave at the surface bounding the second medium and an evanescent wave in the second medium contiguous with the surface;
   (c) locating at least one nanostructure in the second medium proximate the surface where it will encounter the evanescent wave;
   (d) observing at least one effect of electromagnetic interactions between the evanescent wave and the at least one nanostructure; and
   wherein irradiating the waveguide comprises irradiating the waveguide with electromagnetic energy having a free space wave length in the range from 400 nm. to 1000 nm. to create within the first medium a surface wave that is a slow wave having a wavelength that is ten times smaller or less.

15. The method according to claim 14, wherein the electromagnetic energy is blue light having a wavelength in free space of substantially 488 nm.

16. The method according to claim 15, wherein irradiating the waveguide to produce a surface wave comprises directing the blue light toward the surface within the first medium at an angle towards a discontinuity at the surface effective to create the surface wave.

17. The method according to claim 16, wherein the discontinuity is a surface plasmon resonant nanosphere optically coupled by proximity to the waveguide surface.

18. A method of gathering information concerning nanostructure characteristics including:
   (a) providing a waveguide of a first medium having a surface bounding a second medium;
   (b) irradiating the waveguide with an electromagnetic wave to produce a coherent surface wave at the surface bounding the second medium and an evanescent wave in the second medium contiguous with the surface;
   (c) locating at least one nanostructure in the second medium proximate the surface where it will encounter the evanescent wave; and
   (d) observing at least one effect of electromagnetic interactions between the evanescent wave and the at least one nanostructure by providing a reference coherent electromagnetic wave and applying to the reference coherent electromagnetic wave at least one of scattered electromagnetic energy and perturbed electromagnetic energy of the surface wave resulting from impingement of the evanescent wave upon the at least one nanostructure.

19. The method according to claim 18, wherein providing a reference coherent electromagnetic wave comprises splitting the coherent electromagnetic energy irradiating the wave guide and diverting a portion of the electromagnetic energy irradiating the wave guide to produce the reference coherent electromagnetic wave.

20. The method according to claim 19, wherein splitting comprises locating a beam splitter in the path of the evanescent wave in advance of the at least one microstructure to split the evanescent wave into first and second waves, and further including directing the first wave onto the at least one nanostructures, and then to a location of comparative interaction, directing the second wave into the location of comparative interaction to produce at least one of subtractive interference and additive reinforcement between the first and second waves.

21. The method according to claim 20, wherein directing the first wave includes providing a first reflecting mirror in the path of propagation of the first wave intermediate the location of the at least one nanostructure and the location of comparative interaction to direct the first wave to the location of comparative interaction, and providing a second reflective mirror in the path of the second wave intermediate the beam splitter and the location of comparative interaction to direct the second wave to the location of comparative interaction for comparative interaction with the first wave.

22. The method according to claim 21, further comprising locating a detector at the location of comparative interaction to detect the comparative interaction of the first and the second waves.

23. The method according to claim 22, wherein locating a detector at the location of comparative interaction comprises locating a detecting device comprising a series of fluorescent elements at the location of comparative interaction, at least a number of the series of fluorescent elements emitting a fluorescent light of a color differing from other of the fluorescent elements upon fluorescing, each of the number of fluorescent elements having an identified and distinct location relative to the first and second waves, for receiving the first and second waves upon or subsequent to confluence thereof, whereby a color signature caused fluorescing of elements of the detecting device at various locations thereon is indicative of subtractive interference and additive reinforcement of the first and second waves and thereby physical characteristics of the at least one nanostructure.

24. The method according to claim 23, wherein step (a) comprises providing a structure having spaced, conductive particles suspended in a medium of lesser permittivity than the elements.

25. The method according to claim 24, wherein the spaced, conductive particles are gold.

26. The method according to claim 25, wherein the medium of lesser permittivity is $SiO_2$.

27. A method of gathering information concerning nanostructure characteristics including:
(a) providing a waveguide of a first medium having a surface bounding a second medium;
(b) irradiating the waveguide with an electromagnetic wave to produce a surface wave at the surface bounding the second medium and an evanescent wave in the second medium contiguous with the surface;
(c) locating at least one nanostructure in the second medium proximate the surface where it will encounter the evanescent wave; and
(d) observing at least one effect of electromagnetic interactions between the evanescent wave and the at least one nanostructure; and
wherein step (c) comprises moving at least one of the waveguides and the at least one nanostructure to bring the at least one nanostructure from farther into closer proximity with the surface and step (d) comprises-observing the electromagnetic interactions between the evanescent wave and the at least one nanostructure at differing degrees of proximity to the surface.

28. A method of gathering information concerning nanostructure characteristics including:
(a) providing a waveguide of a first medium having a surface bounding a second medium;
(b) irradiating the waveguide with an electromagnetic wave to produce a surface wave at the surface bounding the second medium and an evanescent wave in the second medium contiguous with the surface;
(c) locating at least one nanostructure in the second medium proximate the surface where it will encounter the evanescent wave;
(d) observing at least one effect of electromagnetic interactions between the evanescent wave and the at least one nanostructure; and
wherein the at least one nanostructure comprises a plurality of nanostructures of varying heights, step (c) comprises varying the proximity of the nanostructures to the surface, and step (d) comprises observing the electromagnetic interactions between the evanescent wave and the nanostructures at differing degrees of proximity to the surface.

29. A method of gathering information concerning nanostructure characteristics including:
(a) providing a waveguide of a first medium having a surface bounding a second medium;
(b) irradiating the waveguide with an electromagnetic wave to produce a surface wave at the surface bounding the second medium and an evanescent wave in the second medium contiguous with the surface;
(c) locating at least one nanostructure in the second medium proximate the surface where it will encounter the evanescent wave; and
(d) observing at least one effect of electromagnetic interactions between the evanescent wave and the at least one nanostructure; and
wherein irradiating the waveguide comprises providing a conductive member optically coupled to the waveguide, and illuminating the conductive member with a laser to create a plasmon irradiating the waveguide with coherent light as a substantially point source of light from which the surface wave emanates.

30. The method according to claim 29, further comprising collimating the surface wave emanating from the conductive member.

31. The method of claim 30, further comprising splitting the collimated, coherent surface wave into a reference collimated, coherent surface wave and a collimated, coherent nanostructure illuminating surface wave, illuminating the at least one nanostructure with the collimated coherent nanostructure-illuminating surface wave, and bringing together the reference wave and the nanostructure-illuminating wave for additive reinforcement and subtractive interference indicative of the physical characteristics of the at least one nanostructure.

32. The method of claim 31, further comprising locating a detector at a position where the reference and nanostructure illuminating waves have been brought together to detect the additive reinforcement and subtractive interference of the waves.

33. The method of claim 32, wherein locating a detector comprises providing a series of fluorescent detector particles at locations to be illuminated by the combined reference and nanostructure-illuminating waves, at least a plurality of the fluorescent detector particles at different locations on the detector having differing fluorescent characteristics to thereby emit different wavelengths of light when fluorescing, whereby the wavelengths of light emitted by the detector are indicative of locations on the detector illuminated by the combined reference and nanostructure illuminating waves.

34. The method of claim 33, wherein providing a series of fluorescent detector particles comprises providing the fluorescent detector particles in a linear array across the wavefronts of the combined reference and nanostructure-illuminating waves, the fluorescent characteristics of the fluorescent detector particles differing with differing positions along the array, whereby emissions of light of particular wavelengths by the detector are indicative of additive reinforcement of the reference and the nanostructure illuminating waves upon their being combined at locations across their respective wavefronts.

35. The method of claim 34, wherein the fluorescent detector particles are particles having a cross-sectional dimension in the range from 10 to 100 nm. coated with fluorescent coatings.

36. A structure examination transducer including an electromagnetic illumination pattern detector comprising an array of fluorescent particles, at least a plurality of the particles differing in fluorescent characteristic to emit light of different wavelengths upon fluorescing, means for directing electromagnetic illumination from a structure under examination to the array and means for directing to the array a reference electromagnetic illumination having a frequency causing interfering cancellation and reinforcing enhancement of the illumination from the structure whereby the frequencies of fluorescent emissions from the array are indicative of characteristics of the structure.

37. The transducer of claim 36, wherein the array of fluorescent particles of differing fluorescent characteristics have known locations in the array, whereby emission from the array of light having a profile of varying wavelengths will be indicative of varying illumination of locations on the array.

38. The transducer of claim 37, wherein the emitted light of different wavelengths is visible light exhibiting different colors, whereby the profile of varying wavelengths comprises a combination of colors, each of which is representative of a location on the array.

39. The transducer of claim 37, wherein the array is a linear array of the fluorescent particles, and the emitted light of different wavelengths is indicative of greater and lesser illumination at points along the linear array.

40. The transducer of claim 37, wherein the fluorescent particles are particles coated with fluorescent coatings.

41. The transducer of claim 36, wherein the fluorescent particles are particles of a cross-sectional dimension in a range from 1 to 100 nm.

42. In a transducer for examining nanostructures by irradiating with electromagnetic energy; the improvement including a surface wave conducting waveguide for slowing the speed of electromagnetic energy irradiating the waveguide, and forming the surface wave therein, the waveguide comprising:
(a) an array of spaced conductive metal particles having cross-sectional dimensions in the range from 1 to 100 nm., and spaced 10 to 50 nm. apart,
(b) a binder material of higher dielectric constant coating the particles and filling separations therebetween.

43. The waveguide of claim 42, wherein the binder material is $SiO_2$.

44. The waveguide of claim 42, wherein the particles are gold.

45. The waveguide of claim 44, wherein the binder material is $SiO_2$.

46. The waveguide of claim 42, wherein the particles have a cross-sectional dimension in the range 10 to 50 nm. and are spaced 10 to 50 nm. apart in an array forming with the binder a planar surface for the propagation of a surface wave.

47. A nanostructure examination transducer including:
(a) a waveguide comprising an array of conductive, spaced-apart particles having cross-sectional dimensions in the range 1 to 100 nm. and an interstitial binder having a permittivity greater than that of the particles, said waveguide forming a surface for the propagation of a slow surface wave,
(b) means for coupling a source of radiant energy to the waveguide,
(c) a detector coupled to the waveguide, and
(d) means for locating nanostructures in proximity to the surface to be irradiated by an exponentially decaying evanescent wave associated with a slow surface wave propagated at the surface.

48. The transducer according to claim 47, further comprising:
(e) means for adjusting the relative position of the waveguide surface and the means for locating the nanostructures.

49. The transducer according to claim 47, further comprising a splitter located in a path of propagation of the surface wave for splitting the surface wave into a nanostructure-illuminating wave and a reference wave, a first mirror structure in the path of the first wave to direct the first wave to a location of comparison of the first and second waves and a second mirror structure in the path of the second wave to direct the second wave to the location of comparison and said detector being located to receive recombined first and second wave electromagnetic energy forming patterns of additive reinforcement and subtractive interference indicative of structural characteristics of the nanostructure affecting the first wave.

50. The transducer according to claim 49, wherein the means for coupling a source of radiant energy includes a source of coherent light.

51. The transducer according to claim 50, wherein the source of coherent light is a laser.

52. The transducer according to claim 51, wherein the laser is a source of blue light having a wavelength of substantially 488 nm.

53. The transducer according to claim 51, further comprising a collimating lens for collimating the coherent light prior to its reaching the splitter.

54. The transducer according to claim 47, wherein the means for coupling a source of radiant energy includes a source of light having a wavelength of 400 to 1000 nm. and the waveguide is adapted to slow the light to $\frac{1}{10}$ or less of its speed in free space.

55. The transducer according to claim 54, wherein the particles of the waveguide are spaced apart 1 to 50 nm.

56. The transducer according to claim 55, wherein the particles are gold and the binder is $SiO_2$.

57. A method of displaying characteristics of an object comprising:
(a) illuminating the object with electromagnetic energy;
(b) providing an array of discrete fluorescent units having varying wavelengths of fluorescence when illuminated;
(c) providing a reference illumination of electromagnetic energy illuminating the array;
(d) directing the illuminating electromagnetic energy that has illuminated the object to the array;

whereby fluorescent emissions from the array represent reinforcing combining of the reference illumination and the illuminating electromagnetic energy, and a lack of fluorescent emissions from the array represents a canceling combining of the reference illumination and the illuminating electromagnetic energy.

58. The method according to claim 57, wherein illuminating the object with electromagnetic energy comprises directing electromagnetic energy to a waveguide to produce in the waveguide a surface wave and an evanescent wave extending outwardly of the waveguide, and locating the object for irradiation by an evanescent electromagnetic wave from the waveguide.

59. The method according to claim 58, wherein the object is a nanostructure and step (a) comprises locating the nanostructure proximate a surface of the waveguide, at which the surface wave is produced so as to be irradiated by the evanescent wave.

60. The method according to claim 57, wherein step (c) comprises:

(i) providing a beam splitter; and (ii) illuminating the beam splitter with electromagnetic energy to divide the electromagnetic energy into the reference illumination and illuminating electromagnetic energy.

61. The method according to claim 60, further comprising providing reflecting means for redirecting at least one of the reference illumination and the illuminating electromagnetic energy to the array of discrete fluorescent units.

62. The method according to claim 61, wherein the array of discrete fluorescent units is a linear array.

63. The method according to claim 62, wherein providing reflecting means comprises locating the reflecting means to direct the reference illumination and the illuminating electromagnetic energy to opposite sides of the linear array.

64. The method according to claim 57, wherein the array of discrete fluorescent units is a linear array.

65. The method according to claim 57, wherein steps (a) and (c) directing coherent electromagnetic energy to the object and the array.

* * * * *